(12) United States Patent
Hermanson et al.

(10) Patent No.: US 7,562,541 B2
(45) Date of Patent: Jul. 21, 2009

(54) THERAPEUTIC STOCKING

(75) Inventors: Jon Hermanson, Knoxville, TN (US); Jim Tipton, Kingston, TN (US); Willie York, Harriman, TN (US)

(73) Assignee: Albahealth, LLC, Rockwood, TN (US)

( * ) Notice: Subject to any disclaimer, the term of this patent is extended or adjusted under 35 U.S.C. 154(b) by 127 days.

(21) Appl. No.: 11/607,607

(22) Filed: Dec. 1, 2006

(65) Prior Publication Data

US 2008/0132822 A1 Jun. 5, 2008

(51) Int. Cl.
*D04B 11/34* (2006.01)
(52) U.S. Cl. .................................................. 66/186
(58) Field of Classification Search ............... 66/178 R, 66/183, 184, 185, 186, 187, 182
See application file for complete search history.

(56) References Cited

U.S. PATENT DOCUMENTS

| | | | |
|---|---|---|---|
| 1,811,786 A * | 6/1931 | Frei | ........................ 66/187 |
| 3,975,929 A | 8/1976 | Fregeolle | |
| 4,054,129 A | 10/1977 | Byars et al. | |
| 4,149,274 A | 4/1979 | Garrou et al. | |
| 4,150,442 A | 4/1979 | Boone | |
| 4,153,050 A | 5/1979 | Bishop et al. | |
| 4,153,054 A | 5/1979 | Boone | |
| 4,341,095 A | 7/1982 | Poteat | |
| D275,715 S | 10/1984 | Boone | |
| 4,557,381 A | 12/1985 | Whitney | |
| 4,745,917 A | 5/1988 | Hasty et al. | |
| 5,103,656 A * | 4/1992 | Hanson, II | ................... 66/185 |
| 5,724,836 A * | 3/1998 | Green | ........................ 66/185 |
| 5,814,003 A | 9/1998 | Knox et al. | |
| 6,012,177 A * | 1/2000 | Cortinovis | ................ 66/178 A |
| 6,105,173 A | 8/2000 | Brown | |
| 6,216,495 B1 | 4/2001 | Couzan et al. | |
| 6,371,933 B1 | 4/2002 | Gardon-Mollard | |
| 6,708,348 B1 * | 3/2004 | Romay | ........................ 2/239 |
| 7,007,517 B2 * | 3/2006 | Menzies | ...................... 66/185 |

* cited by examiner

*Primary Examiner*—Danny Worrell
(74) *Attorney, Agent, or Firm*—Baker Donelson et al.

(57) ABSTRACT

A therapeutic compression stocking is knitted in an integrated knit format to have an oversized heel pocket from which an ankle arch portion extends that is knitted in a rib stitch format that is free of wrinkles when donned. The foot and leg are of conventional compression stocking construction.

2 Claims, 3 Drawing Sheets

THERAPEUTIC STOCKING

TECHNICAL FIELD

This invention relates generally to therapeutic stockings and more specifically to compression stockings that are produced in an integrated knit stitch format.

BACKGROUND OF THE INVENTION

Heretofore compression stockings have been designed to address specialized needs of both athletes and medical patients. Venous disorders provide the most prevalent need today for such stockings. More specifically, they have been designed and developed to apply different degrees of pressure to different portions of the body parts over which they are worn for enhanced venal flow. Exemplary of such compression stockings are those described and shown in U.S. Pat. Nos. 4,745,917, 6,012,177, 6,105,173, 6,216,495 and 6,371,933.

With some compression stockings however excessive stress is produced on the yarns and knit structures in the heels of the stockings while being donned. In other cases wrinkling occurs in the foot crest or arch of the stocking over the ankle circumferentially opposite the heel once the stocking has been donned This can cause dermatological irritation which is commonly known as necrosis or skin shearing. These problems have been addressed by providing a stocking gap in the area of the heel. However this, of course, exposes the heel and stresses the gap boundary of the stocking stitching. In other cases one or more patches have been sewn into these problem areas. This approach however negates the stocking from being produced in an integrated knit stitch format with its attendant manufacturing efficiency. It also fails to produce a seamless product.

SUMMARY OF THE INVENTION

In a preferred form of the invention a therapeutic compression stocking is efficiently produced in an integrated knit stitch format which provides less compression on the heal when worn than on the leg or foot without the formation of wrinkles in the foot arch area. To this end the stocking is knitted with an integrated knitting machine to have a heel pocket that is oversized by loosening the loops of the knit loops here. It is also knitted with a stitch format in the ankle crest or arch area that does not substantially wrinkle over the ankle arch when worn. This is done by having the stitch format here in a pattern of ribs that extend between leg and foot portions of the stocking as an arch that is knitted directly or indirectly to the oversized heel pocket and to the foot and leg portions.

DETAILED DESCRIPTION

Figure 1:
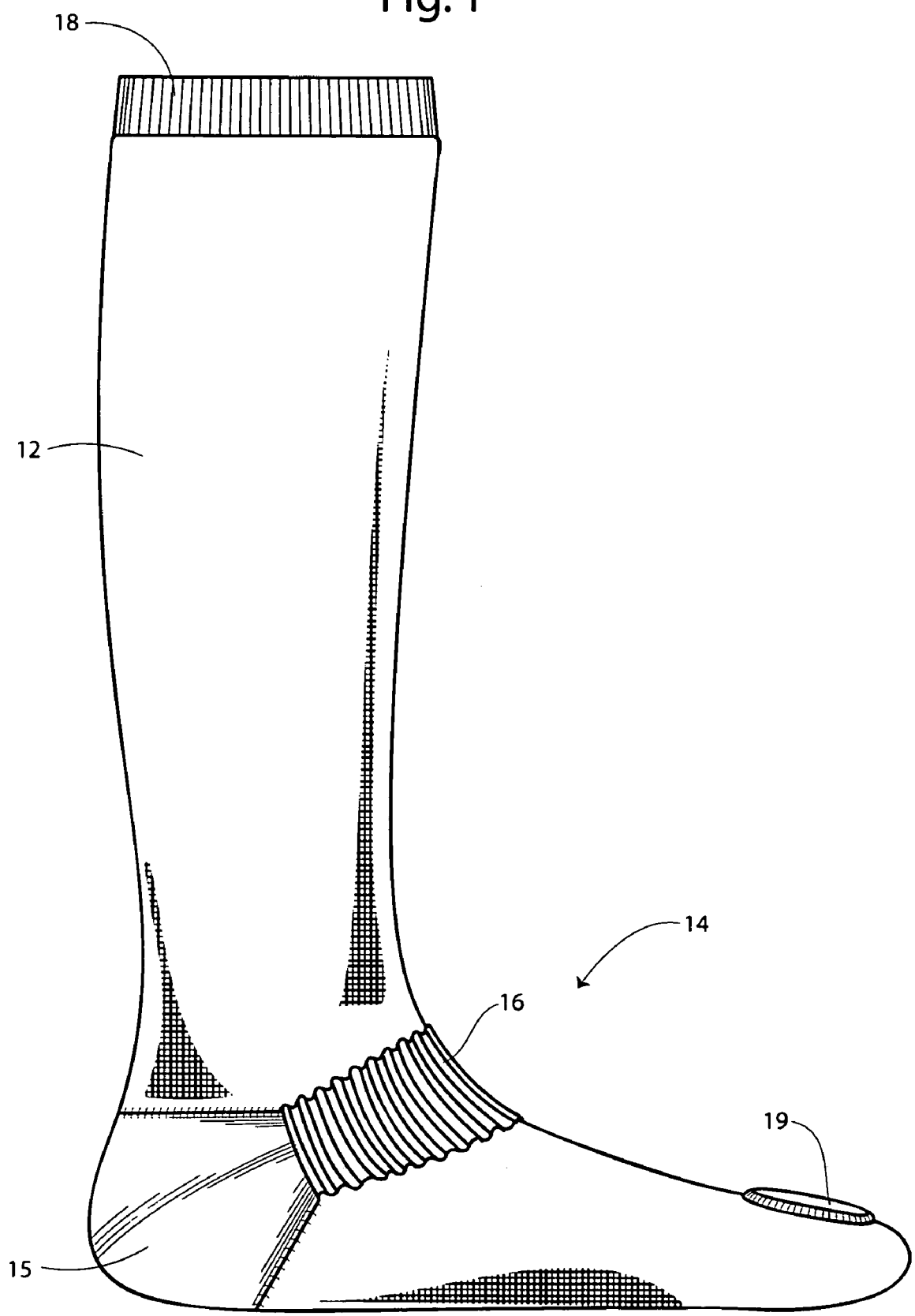
FIG. 1 is a side view of a preferred form of the stocking shown in a worn state, the opposite side being substantially a mirror image thereof.

With reference next to the drawing the therapeutic compression stocking 10 is seen to have a leg portion 12 joined to a foot portion 14 by a heel pocket 15 and an ankle crest or arch portion 16. The leg portion may be of various lengths such as to end below or above the knee at a cuff 18. The top of the foot portion is formed with an opening above the toes bounded by a cuff 19. The stocking may, of course, be produced in any number of overall sizes to fit patients of different sizes.

The stocking is efficiently produced in an integrated knit stitch format with a knitting machine that has needle by needle selection capability. Exemplary of such commercial knitting machines are the Lonati Models 304 and 404. Such a machine can change the stitching needle by needle as the stocking is knitted in tubular from one end to another. The machine thus can be programmed to alter the stitch format from one portion of the stocking to another with yarns extending continuously from one stocking end to the other. Thus the stocking can be made seamless.

With continued reference to the drawing, the leg portion 12 is conventionally knitted in a graduated compression format so that it is tightest when donned at its lower end and gradually becomes less tight higher up the leg. This serves to force blood towards the cardiac cavity of the patient The foot portion 14 is also of a conventional compression knit construction.

The heel pocket 15 here is knitted so as to be oversized relative to the foot and leg portions. This is done by programming the machine to loosen and open up each knitted loop of the stitching. Conversely, an oversized heel has traditionally been formed as a patch with similar relaxed and cross stretch properties as the balance of the stocking in the area adjacent to the heel. This, of course, requires patching to be introduced into the overall manufacturing process which impedes efficiency of production and introduces seams.

By the heel being oversized relative to other portions of the stocking, when the stocking is laid out as a flat tubular blank, the heel is slightly wrinkled. The stitch loops of the oversized heel pocket are knitted looser than the stitch loops of the leg and foot portions so as to have some one-third or more elongation than these other portions. This serves to facilitate donning where the outcropped heel provides a donning impediment. This is especially beneficial where a wound dressing has been applied to the patient's heel. This construction also insures that minimal tension is placed on the yarns of the heel pocket while the stocking is being donned.

Figure 2:
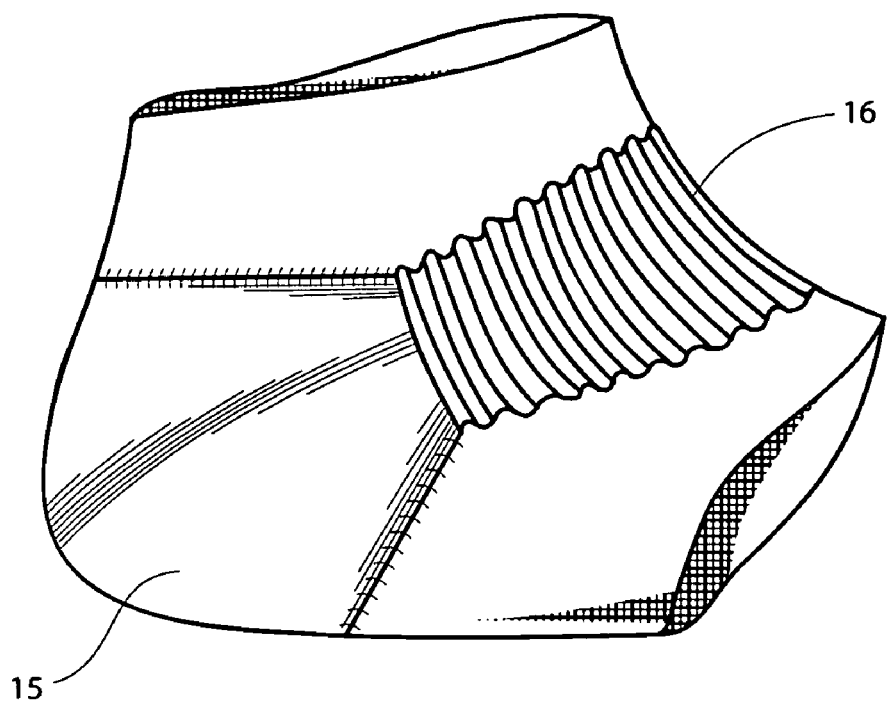
FIG. 2 is an enlarged view of a portion of the stocking shown in FIG. 1.
Figure 3:
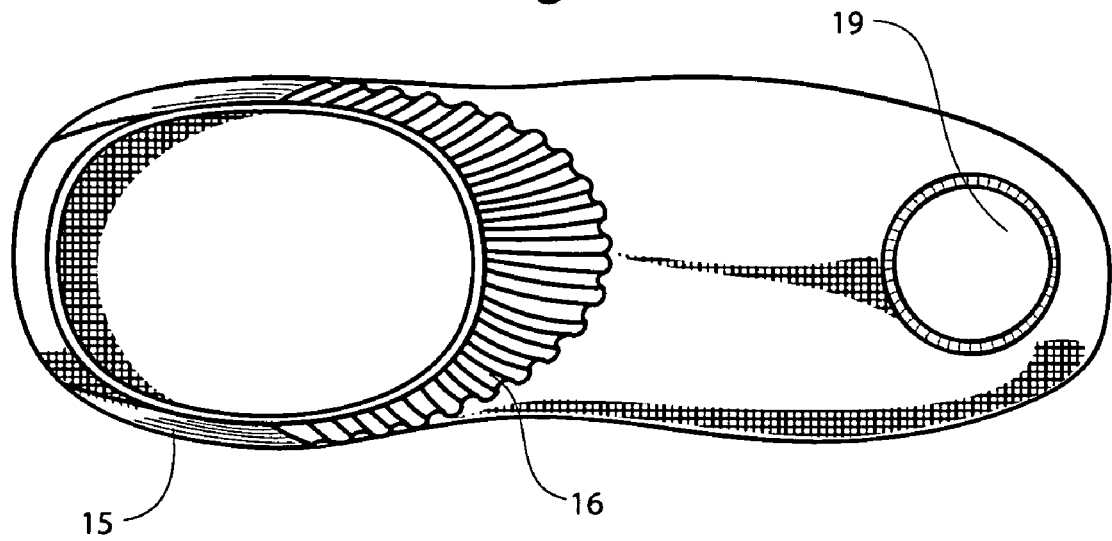
FIG. 3 is a top view of the stocking shown in FIG. 1.

The ankle crest or arch portion 16 is knitted in a manner that substantially prevents it from wrinkling when donned as would occur if it were of the same stitch format as that of the heel pocket, leg or foot portion. This is achieved by programming the knitting machine to gather the excess stitches here into a multi-ribbed format as shown most clearly in FIG. 2. Once donned the gathered ribs become ungathered and smooth without wrinkles. Otherwise, were wrinkles to remain here the skin beneath this arch would become subject to abrasion.

Figure 4A:
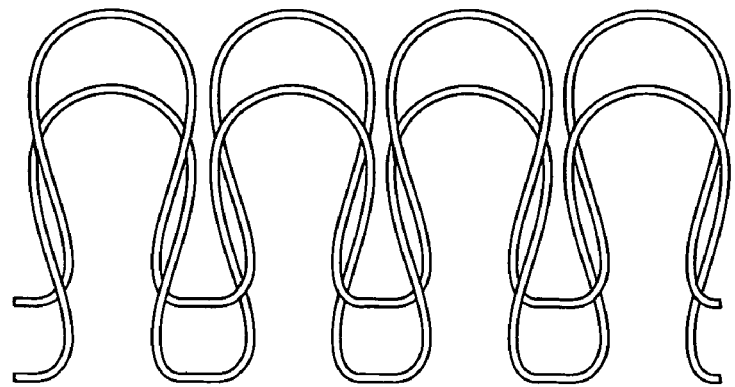
FIGS. 4A-4C illustrated 1×1, 2×2 and 3×1 knit rib formats, respectively.
Figure 4B:
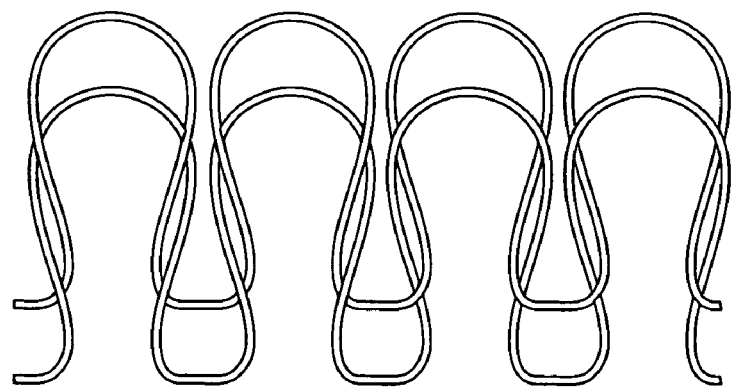
Figure 4C:
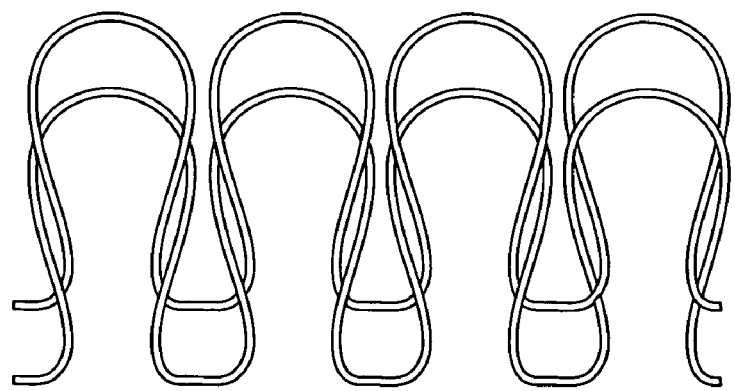

The ankle arch portion is preferably knitted in a 1×1, a 2×2 or a 3×1 rib format, depending on the thermo-plastic properties, modulus and size of the yarns. These formats are illustrated in FIGS. 4A-4C. In FIG. 4A it is seen that alternating wales are looped to the front and then to the back. As viewed here from left to right, the upper loop is over the top of the lower. The next loop is under, the next over, the next under, and so forth. This is a 1×1 format. In FIG. 4B every two adjacent wales are looped over and the next two under, again as viewed from left to right. This is a 2×2 format. FIG. 4C shows a 3×1 rib format or structure where three wales are looped over and then one wale is looped under, and so forth. Preferably the ankle arch portion is knitted directly to the heel pocket although this is not essential.

The preferred stocking yarns here are stretch nylon and spandex, spandex being an elastic fiber sold under the trade name LYCRA and available from E. I. DuPont de Nemours and Company, Wilmington, Del., U.S.A. Stretch nylon and spandex are synthetic fibers that are resilient. Their degree of stretch and recovery can be thermally altered to a desired modulus.

Preferably the foot cuff 18 and heel border are color coded for ease in orienting the stocking for donning. This contrasting color can be provided topically or by differentiating yarn color selection.

The term wrinkle is intended to mean unintended bends or crimps in yarn, mis-shaped stitches, or excess material that adversely affects the presentation, hand, or performance of a fabric or the end product.

It thus is seen that a therapeutic compression stocking may now be manufactured in an integrated knit stitch format that my be donned with facility over the heel and which provides improved graduated pressure between the heel and the leg and foot portions all without wrinkling of the stocking over the ankle arch. Although the stocking has been illustrated and described in its preferred form, it should be understood that many modifications, additions and deletions may be made to that specific form without departure from the spirit and scope of the invention as set forth in the following claims.

The invention claimed is:

1. A therapeutic compression stocking having tubular knitted yarn foot and leg portions joined by a knitted yarn foot arch portion and a heel pocket, and wherein said foot and leg portions are knitted with a knit format having a first yarn density, wherein said foot arch portion is knitted with a knit format having a second yarn density greater than said first yarn density, and wherein said heel pocket is knitted with a knit format having a third yarn density greater than said first yarn density.

2. The therapeutic compression stocking of claim 1 wherein said foot arch portion is knitted in a multi-ribbed format to achieve said second yarn density.

* * * * *